United States Patent [19]

Perrone et al.

[11] Patent Number: 4,863,914
[45] Date of Patent: Sep. 5, 1989

[54] PENEM DERIVATIVES

[75] Inventors: Ettore Perrone; Marco Alpegiani; Angelo Bedeschi, all of Milan; Franco Zarini, Settimo Milanese; Giovanni Franceschi, Milan; Costantino D. Bruna, Rho, all of Italy

[73] Assignee: Farmitalia Carlo Erba, Milan, Italy

[21] Appl. No.: 849,387

[22] Filed: Apr. 8, 1986

[30] Foreign Application Priority Data

Apr. 10, 1985 [GB] United Kingdom ............... 8509180

[51] Int. Cl.[4] ............... C07D 499/00; A61K 31/425
[52] U.S. Cl. ............................... 514/192; 514/195; 540/310
[58] Field of Search ............... 540/225, 310; 514/192, 514/193, 195

[56] References Cited

U.S. PATENT DOCUMENTS 4,577,016  3/1986  Alpegiani et al. ............... 540/310
4,623,643 11/1986  Alpegiani et al. ............... 540/310

FOREIGN PATENT DOCUMENTS 0070204  1/1983  European Pat. Off. .
0110826 10/1983  European Pat. Off. .
0125207  4/1984  European Pat. Off. .
2042515  9/1980  United Kingdom .

Primary Examiner—Nicholas S. Rizzo
Attorney, Agent, or Firm—Oblon, Spivak, McClelland, Maier & Neustadt

[57] ABSTRACT

Compounds of formula

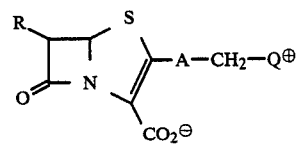

wherein R is hydrogen atom or $C_1$–$C_4$ alkyl group optionally substituted from halogen atom or hydroxy group optionally protected, A is a Z, Z—O—C—O— or Z—C)— residue, wherein Z is phenylene, naphthylene, heterocyclediyl, $C_1$–$C_7$ alkylene, $C_2$–$C_4$ alkenylene, alkynylene,

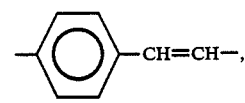

$C_3$–$C_8$ cycloalkylene, aralkylene radical optionally substituted, and $O^{(+)}$ represents a group $+NR_1R_2R_3$, wherein $R_1$, $R_2$ and $R_3$ are each either:

(i) a optionally substituted alkyl, aralkyl or aryl radical or
(ii) $R_1$ is as defined above under (i) and $R_2$ and $R_3$, taken together, represent an optionally substituted or fused heterocyclic radical, or
(iii) $R_1$, $R_2$ and $R_3$, taken together, represent an optionally substituted azonia-bicyclo or tricyclo radical, or
(iv) $R_1$, $R_2$ and $R_3$, taken together, represent an optionally substituted or fused pyridinium, pyrazinium, pyrazolium or pyridazinium radical, and the pharmaceutically or veterinarily acceptable salts thereof, are disclosed.

A method of preparation is also provided. The compounds show high antibacterial activity.

26 Claims, No Drawings

PENEM DERIVATIVES

BACKGROUND OF THE INVENTION

1. Field of the Invention

The present invention relates to penem compounds, to processes for their preparation, and to pharmaceutical and veterinary compositions containing penem compounds.

2. Description of the Background

Penem compounds are antibiotics. There is a continuing need for new antibiotics because the continued wide scale use of these compounds gives rise to resistant strains of pathogens. Accordingly, there is no constant effectiveness for any given antibiotic. Additionally, known antibiotics suffer from the disadvantage of being effective against only certain types of microorganisms.

There is thus a strongly felt need for new antibiotics which do not suffer from the above disadvantages.

SUMMARY OF THE INVENTION

Accordingly, it is an object of this invention to provide a novel class of antibiotics.

It is another object of this invention to provide a novel class of antibiotics which are useful in human therapy.

It is another object of this invention to provide a novel class of antibiotics which are useful in animal therapy.

It is another object of this invention to provide a novel class of antibiotics which are potent antibacterial agents.

It is another object of this invention to provide a novel class of antibiotics which are broad spectrum antibacterial agents.

It is another object of this invention to provide a novel class of antibiotics which are imbued with increased activity against Gram-positive strains.

It is another object of this invention to provide a novel class of antibiotics which are imbued with increased activity against Gram-negative strains.

It is another object of this invention to provide a novel class of antibiotics which have prolonged plasma levels.

It is another object of this invention to provide a novel class of antibiotics which display a very high degree of therapeutic effectiveness in treating infections caused by both Gram-positive and Gram-negative bacteria.

It is another object of this invention to provide a novel class of antibiotics having negligible toxicity.

It is another object of this invention to provide a novel class of antibiotic compounds which are useful in the treatment of respiratory tract infections; e.g., bronchitis, bronchopneumonia or pleuritis.

It is another object of this invention to provide a novel class of antibiotic compounds which are useful in the treatment of hepatobiliary or abdominal infections.

It is another object of this invention to provide a novel class of antibiotic compounds which are useful in the treatment of septicemia.

It is another object of this invention to provide a novel class of antibiotic compounds which are useful in the treatment of urinary tract infections; e.g., pyelonephritis or cystitis.

It is another object of this invention to provide a novel class of antibiotic compounds which are useful in the treatment of obstetrical and gynecological infections; e.g., cervicitis or endometritis.

It is another object of this invention to provide a novel class of antibiotic compounds which are useful in the treatment of ear, nose and throat infections; e.g., otitis, sinusitis or parotitis.

It is another object of this invention to provide a novel method for the treatment of respiratory tract infections, hepatobiliary and abdominal infections, septicemia, urinary tract infections, obstetrical and gynecological infections, or ear, nose and throat infections.

The inventors have now discovered a novel class of penem antibiotics which surprisingly satisfy all of the above objects of this invention as well as other objects which will become apparent from the description of this invention given hereinbelow. The present invention thus relates to new penem compounds, to processes for their preparation, and to pharmaceutical and veterinary compositions containing them.

The compounds of the invention are quaternary ammonium carboxylates of the following formula (I) and their pharmaceutically or veterinarily acceptable salts

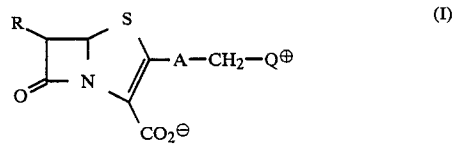

wherein

R is a hydrogen atom or a $C_1$-$C_4$ alkyl group which may be either unsubstituted or substituted by one or more substituents chosen from free or protected hydroxy groups and halogen atoms;

A is a Z, Z—O—CO— or —Z—CO— residue, wherein Z represents (a) an unsubstituted or substituted phenylene or naphthylene group; (b) an unsubstituted or substituted heterocyclediyl radical where the hetero ring is mono or bicyclic, saturated or unsaturated, and contains at least one heteroatom selected from the group of oxygen, sulphur and nitrogen atoms; (c) an unsubstituted or substituted linear or branched $C_1$-$C_7$ alkylene radical; (d) a $C_2$-$C_4$ alkenylene or alkynylene group or a group of formula:

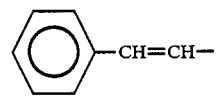

or (e) an unsubstituted or substituted $C_3$-$C_8$ cycloalkylene ring; (f) an aralkylene radical of formula:

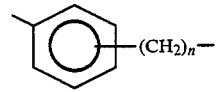

wherein n is 1, 2 or 3, and Q(+) represents a +$NR_1R_2R_3$ group, wherein (i) $R_1$, $R_2$ and $R_3$ are each independently an unsubstituted or substituted alkyl, aralkyl or aryl radical; or (ii) $R_1$ is as defined above under (i) and $R_2$ and $R_3$ taken together with the nitrogen atom to which they are both bound represent an unsubstituted or substituted heterocyclic or fused heterocyclic radical; or (iii) $R_1$, $R_2$ and $R_3$ taken together with the nitrogen atom to which they are all bound represent an unsubstituted or substituted azoniabicyclo or azoniatricyclo radical; or (iv) $R_1$, $R_2$ and $R_3$ taken together with the nitrogen atom to which they are all bound represent an unsubstituted or substituted pyridinium, pyrazinium, pyrazolium, or pyridazinium radical, or an unsubstituted or substituted pyridinium, pyrazinium, pyrazolium, or pyridazinium radical fused with one phenyl ring or with a 5 to 7 membered, saturated or unsaturated cycloaliphatic or heterocyclic ring.

The present invention includes all the possible geometrical and optical isomers of the compounds of formula (I). They may be in the form of isomeric mixtures or in the form of the individual separated isomers. Preferably, the compounds of formula (I) have a (5R, 6S) configuration. The preferred R group is an (α-hydroxy)ethyl radical. This radical preferably has a (1R) configuration, i.e., a R configuration at the α-carbon atom of the ethyl group.

As noted above the pharmaceutically or veterinarily acceptable salts of the compounds of formula (I) are included within the scope of this invention. These salts may be both salts with (1) acids; any pharmaceutically or veterinarily acceptable inorganic or organic acids such as, e.g., hydrochloric, hydrobromic, sulfuric, or phosphoric acid, or acetic, citric, tartaric, fumaric or methanesulphonic acid, and salts with (2) any pharmaceutically or veterinarily acceptable bases; either inorganic bases such as, e.g., alkali or alkaline-earth metal hydroxides, in particular sodium and potassium hydroxides, or organic bases such as, e.g., triethylamine, pyridine, benzylamine or collidine, including aminoacids such as, e.g., lysine or procaine. The invention includes also inner salts, i.e., zwitterions. In the present specification, the term "halogen" encompasses fluorine, chlorine, bromine and iodine atoms, preferably fluorine and chlorine atoms.

DETAILED DESCRIPTION OF THE PREFERRED EMBODIMENTS

The alkyl groups, including the aliphatic moieties of the alkoxy, alkylthio and alkanoyl groups, may be branched or straight chain. Preferably, the alkyl and aralkyl radicals under definition (i) for Q are unsubstituted or substituted $C_1-C_4$ alkyl and $C_7-C_{11}$ aralkyl radicals. In the definitions of Z, $R_1$, $R_2$ and $R_3$, the substituents for the mentioned alkyl, aralkyl, aryl, azoniabicyclo, azoniatricyclo, pyridinium, pyrazinium, pyrazolium, pyridazinium, cycloalkylene, alkylene, phenylene, naphthylene and heterocyclediyl radicals are preferably selected from the group consisting of: (a) halogens; (b) hydroxy; (c) $C_1-C_4$ alkoxys; (d) $C_1-C_4$ alkylthios; (e) a group —$NR_4R_5$, wherein $R_4$ and $R_5$ is, independently, a hydrogen atom or a $C_1-C_4$ alkyl groups; (f) sulfos; (g) —$CO_2R_4$ groups, wherein $R_4$ is as defined above; (h) —CN; (i) dimethylformimidino; (j) —CO—$NR_4R_5$, groups wherein $R_4$ and $R_5$ are as defined above; (k) hydroxycarbamoyl or carbamoyloxy groups; (l) hydroxyiminomethyl (HO—N=CH—) or methoxyiminomethyl ($CH_3$O—N=CH—) groups, hydroxyimino (α-methyl)methyl (HO—N=C($CH_3$)—) groups; (m) formamido or acetamido groups; (n) formyloxy or acetoxy groups; (o) $C_1-C_4$ alkanoyl groups; (p) aryl groups; (q) saturated or unsaturated heterocyclic rings; (r) a nitro group; (s) a mesyloxy group; (t) oxo groups; and (u) $C_1-C_4$ alkyl groups which may be either unsubstituted or substituted by a substituent chosen from (a) to (t) above.

A $C_1-C_4$ alkyl group is, preferably, a methyl or an ethyl group.

A heterocyclediyl radical is, preferably, a furanediyl, a 1,3-thiadiazolediyl, a thiophenediyl or a pyridinediyl group.

A $C_1-C_7$ alkylene radical is preferably a methylene, an ethylene, a propylene or a butylene group.

A $C_3-C_8$ cycloalkylene ring is, preferably, a cyclobutylene, a cyclopentylene or a cyclohexylene group.

A $C_2-C_4$ alkenylene group is, preferably, a 1,2-ethenylene group.

A $C_2-C_4$ alkynylene group is, preferably, an ethynylene group.

The term "aryl" encompasses, preferably, phenyl and naphthyl groups. The heterocyclic rings may be saturated or unsaturated. They may have from 4 to 7 members. And they may contain from 1 to 4 heteroatoms selected from oxygen, nitrogen and sulphur atoms.

A $C_1-C_4$ alkoxy group is, preferably, a methoxy or an ethoxy group.

A $C_1-C_4$ alkylthio group is, preferably, a methylthio or an ethylthio group.

A $C_1-C_4$ alkanoyl group is, preferably, an acetyl or a propionyl group.

A protected hydroxy group may be a hydroxy group protected by a protecting group chosen from for instance, an unsubstituted or substituted, especially halo-substituted, acyl group, e.g., acetyl, monochloroacetyl, dichloroacetyl, trifluoroacetyl, benzoyl or p-bromophenacyl; a triarylmethyl group, in particular triphenylmethyl; a silyl group, in particular trimethylsilyl, dimethyl-tert-butylsilyl, diphenyl-tert-butyl silyl; or also a group such as tert-butoxycarbonyl, p-nitro-benzyloxycarbonyl, 2,2,2-trichloroethoxycarbonyl, allyloxycarbonyl, benzyl, and pyranyl.

Preferred protecting groups of the hydroxy function are p-nitro-benzyloxycarbonyl; dimethyl-tert-butylsilyl; diphenyl-tert-butyl-silyl; trimethyl silyl; allyloxycarbonyl; benzyl; p-bromophenacyl; triphenylmethyl and pyranyl.

Preferred classes of compounds under this invention include compounds of formula (I) wherein:
R is an (α-hydroxy)ethyl group;
Z is one of the following residues:

(a') 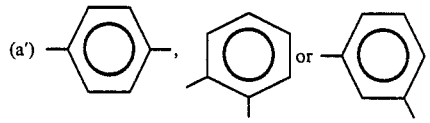

(b') 

(c') a methylene, an ethylene, a n-propylene or a tetramethylene group (d') a 1,2-ethenediyl group;

(e') 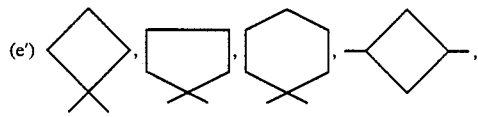

-continued

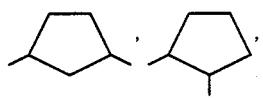

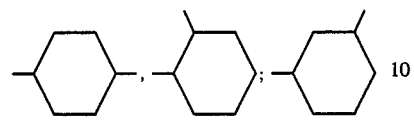

(f') para, meta or ortho

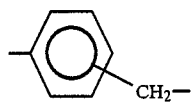

$Q^{(+)}$ is $+NR_1R_2R_3$, wherein
(i') $R_1$, $R_2$ and $R_3$ are each independently a methyl, an ethyl, a n-propyl, an i-propyl, a dimethylaminomethyl, or cyanomethyl, a cyanoethyl, a carbamoylmethyl, a 2-hydroxyethyl, a 2-cloroethyl, a carboxymethyl, an ethoxycarboxylmethyl, a carboxyethyl, a 2-methyl-2-cyanoethyl, a 3-oxobutyl or a dimethylformimidino group —C(NMe₂)═NH; or
(ii') $R_1$ is as defined above under (i'), still preferably a methyl, an ethyl, a chloroethyl, a cyanomethyl, a cyanoethyl, a hydroxyethyl or an aminoethyl, and $R_2$ and $R_3$, taken together with the nitrogen atom to which they are bound, represent one of the following heterocyclyl ammonium radicals;

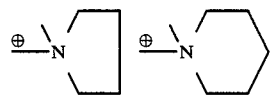

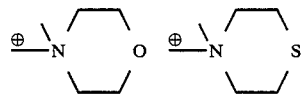

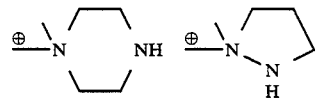

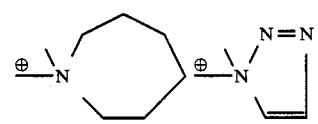

The above heterocyclic rings maybe unsubstituted or substituted. When they are substituted, the substituted are one or more, preferably one or two substituents, which may be the same or different and selected form the group (a), (b), (e), (g), (h), (i), (q), (t) and (u) as defined above; or (iii') $R_1$, $R_2$ and $R_3$, taken together with the nitrogen atom to which they are all bound, represent one of the following radicals;

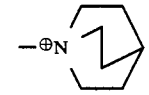

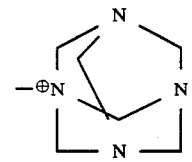

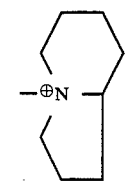

wherein the quinuclidine ring may be substituted by an oxo, hydroxy or methoxy group; or (iv') $R_1$, $R_2$ and $R_3$, taken together with the nitrogen atom to which they are all bound, represent one of the following radicals;

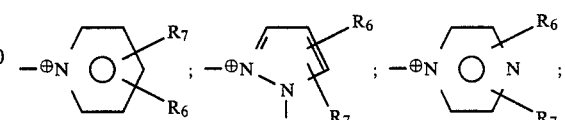

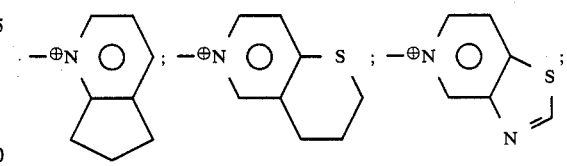

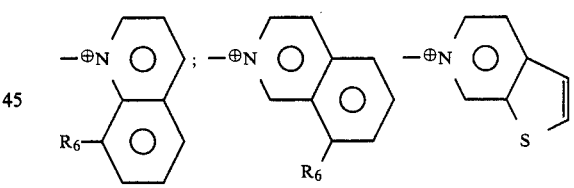

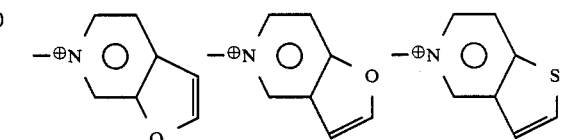

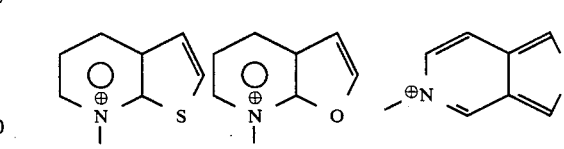

wherein $R_6$ and $R_7$ are independently a hydrogen atom; a C₁-C₄ alkyl, which may be unsubstituted or substituted with a cyano, a hydroxy, a sulfo, a hydroxyimino group; a methylsulphonyl; a carbamoyl; a hydroxy; a methylthio; a methoxy; a formamido; a formyl; a hydroxycarbamoyl or an amino group, and the pharmaceutically or veterinarily acceptable salts thereof.
Specific examples of preferred compounds of the invention are listed in the following table:
| COMPOUND | —A— | —Q⊕ |
|---|---|---|
| 1 |  | —⊕N⟨pyrrolidine⟩ CH₃ |
| 2 | 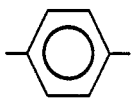 | —⊕N⟨piperidine⟩ CH₃ |
| 3 | 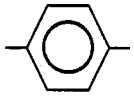 | —⊕NMe₃ |
| 4 |  | —⊕NEt₃ |
| 5 |  | —⊕N⟨pyridine⟩ |
| 6 |  | —⊕N⟨cyclopentapyridine⟩ |
| 7 | | —⊕N⟨pyridine⟩—CONH₂ |
| 8 | | —⊕N⟨pyridine with C₂H₅ and CH₃⟩ |
| 9 | | —⊕N⟨quinoline⟩ |

-continued

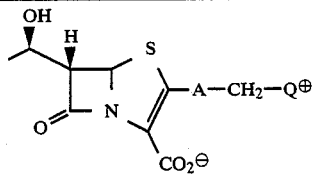

| COMPOUND | —A— | —Q⊕ |
|---|---|---|
| 10 | *para-phenylene* | *1-azabicyclo[2.2.2]octane (quinuclidinium)* |
| 11 | *para-phenylene* | *N-methylmorpholinium* |
| 12 | *para-phenylene* | *N-methylpiperazinium (NH)* |
| 13 | *para-phenylene* | *N,N'-dimethylpiperazinium* |
| 14 | *meta-phenylene* | *pyridinium* |
| 15 | *meta-phenylene* | *isoquinolinium* |
| 16 | *meta-phenylene* | *3-(cyanomethyl)pyridinium* |
| 17 | *meta-phenylene* | *pyrazinium* |
| 18 | *meta-phenylene* | —NMe₃⊕ |
| 19 | *meta-phenylene* | —NEt₃⊕ |

-continued
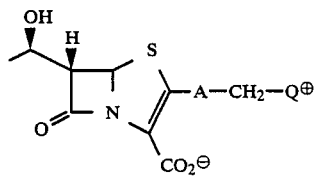
| COMPOUND | —A— | —Q⊕ |
|---|---|---|
| 20 | 2,3-dimethylphenyl | N-methylpyrrolidinium |
| 21 | 2,3-dimethylphenyl | N-methylpiperidinium |
| 22 | 3,5-dimethylphenyl | pyridinium |
| 23 | 3,5-dimethylphenyl | N-methylpyrrolidinium |
| 24 | 3,5-dimethylphenyl | —NMe₃⊕ |
| 25 | 3,3-dimethylcyclopentyl | pyridinium |
| 26 | 3,3-dimethylcyclopentyl | N-methylpyrrolidinium |
| 27 | 3,3-dimethylcyclopentyl | —NEt₃⊕ |
| 28 | 2,5-thienyl | N-methylpyrrolidinium |
| 29 | —CH₂CH₂— | pyridinium |

-continued
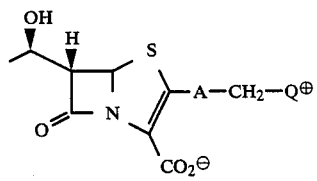
| COMPOUND | —A— | —Q⊕ |
| --- | --- | --- |
| 30 | —CH₂CH₂— | 3-(cyanomethyl)pyridinium |
| 31 | —CH₂CH₂— | 1-methylpyrrolidinium |
| 32 | —CH₂CH₂— | —N⊕Me₃ |
| 33 | —CH₂CH₂CH₂— | 3-(cyanomethyl)pyridinium |
| 34 | —CH₂CH₂CH₂— | pyridinium |
| 35 | —CH₂CH₂CH₂— | 1-methylpyrrolidinium |
| 36 | cyclobutane-1,3-diyl | —N⊕(CH₃)₃ |
| 37 | cyclopentane-1,3-diyl | pyridinium |
| 38 | trans-CH=CH | pyridinium |
| 39 | cis-CH=CH | pyridinium |
| 40 | cis-CH=CH | 1-methylpyrrolidinium |

-continued
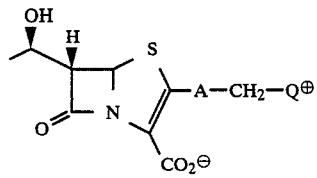
| COMPOUND | —A— | —Q⊕ |
|---|---|---|
| 41 | —CH₂OC(=O)— | N-methylpyrrolidinium |
| 42 | —CH₂CH₂—OC(=O)— | pyridinium |
| 43 | —CH₂CH₂—OC(=O)— | N-methylpyrrolidinium |
| 44 | 1,4-phenylene-C(=O)— | pyridinium |
| 45 | 1,3-phenylene-C(=O)— | pyridinium |
| 46 | 1,4-phenylene-CH₂-C(=O)— | pyridinium |
| 47 | 1,4-phenylene | 3-(methylthio)pyridinium |
| 48 | 1,4-phenylene | 4-(methylthio)pyridinium |
| 49 | 1,4-phenylene | 3-methoxypyridinium |
| 50 | 1,4-phenylene | 4-methoxypyridinium |

-continued
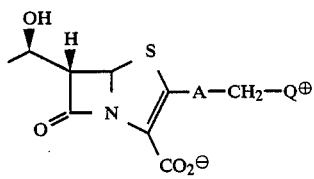
| COMPOUND | —A— | —Q⊕ |
|---|---|---|
| 51 | (p-phenylene) | pyridinium-2-OCH₃ |
| 52 | cis-CH=CH | 1-methylpyrrolidinium |
| 53 | cis-CH=CH | pyridinium-3-OCH₃ |
| 54 | (p-phenylene) | 3,5-dimethylpyridinium |
| 55 | (p-phenylene) | pyridinium-3-OH |
| 55/a | (p-phenylene) | pyridinium-3-CH₂CH₂SO₃⁻ |
| 56 | (p-phenylene) | pyridinium-3-CH₂OH |
| 57 | (p-phenylene) | pyridinium-2-CH₂CH₂OH |
| 58 | (p-phenylene) | 1-methyl-8-hydroxyquinolinium |

-continued

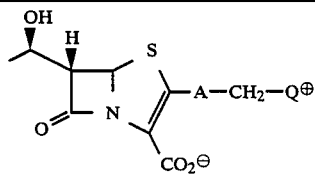

| COMPOUND | —A— | —Q⊕ |
|---|---|---|
| 59 | —C₆H₄— (para) | N-methyl 8-hydroxyisoquinolinium |
| 60 | —C₆H₄— (para) | 3-(NHCHO)-pyridinium, N-methyl |
| 61 | —C₆H₄— (para) | 4-(CONHOH)-pyridinium, N-methyl |
| 62 | —C₆H₄— (para) | 3-CHO-pyridinium, N-methyl |
| 63 | —C₆H₄— (para) | 3-(CH=NOH)-pyridinium, N-methyl |
| 64 | —C₆H₄— (para) | 4-(C(Me)=NOH)-pyridinium, N-methyl |
| 65 | —C₆H₄— (para) | 3-NH₂-pyridinium, N-methyl |
| 66 | —C₆H₄— (para) | N-methyl pyrazinium |
| 67 | —C₆H₄— (para) | 1-methyl-1,2,3-triazolium |
| 68 | —C₆H₄— (para) | 1-methyl pyrazolium |

-continued

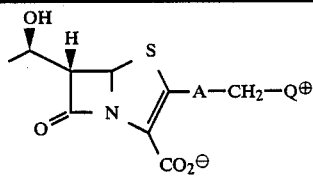

| COMPOUND | —A— | —Q⊕ |
|---|---|---|
| 69 | -phenylene- | N-methyl thieno[2,3-b]pyridinium |
| 70 | -phenylene- | N-methyl furo[2,3-b]pyridinium |
| 71 | -phenylene- | N-methyl furo[3,2-b]pyridinium |
| 72 | -phenylene- | N-methyl thieno[3,2-b]pyridinium |
| 73 | -phenylene- | N-methyl thieno[2,3-b]pyridinium (N-alkylated) |
| 74 | -phenylene- | N-methyl furo[2,3-b]pyridinium (N-alkylated) |
| 75 | -phenylene- | N-methyl thieno[3,4-c]pyridinium |
| 76 | -phenylene- | N-methyl thiazolo[5,4-c]pyridinium |

The compounds of formula (I) can be prepared by a process comprising reacting a compound of formula (II)

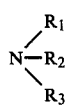

wherein $R_1$, $R_2$ and $R_3$ are as defined above, with a penem intermediate of formula (III)

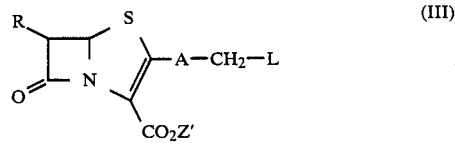

wherein R and A are as defined above, Z' is a carboxy protecting group, and L is a leaving group susceptible to nucleophilic displacement by the amine of formula (II). The protecting groups present are then removed and, if desired, a mixture of isomers obtained is separated into the single isomers.

The leaving group L in the compound of formula (III) may be, for example, a sulphonyloxy group —O—SO$_2$R', wherein R' is an unsubstituted or substituted alkyl group or an aryl group; or a halogen atom such as iodine, bromine or chlorine. A particularly preferred sulphonyloxy group is trifluoromethanesulphonyloxy, —OSO$_2$CF$_3$. A particularly preferred halogen atom is iodine.

A carboxy protecting group Z' may be any group which, together with the —CO$_2$— moiety, forms an esterified carboxy group. Examples of carboxy protecting groups are, in particular, C$_1$-C$_6$ alkyl groups, for instance methyl, ethyl or tert-butyl; halosubstituted C$_1$-C$_6$ alkyl groups, for example 2,2,2-trichloroethyl; C$_2$-C$_4$ alkenyl groups, for example allyl; unsubstituted or substituted aryl groups, for example phenyl and p-nitro-phenyl; unsubstituted or substituted aryl C$_1$-C$_6$ alkyl groups, for example benzyl, p-nitro-benzyl and p-methoxy-benzyl; aryloxy-C$_1$-C$_6$ alkyl groups, for example phenoxy-ethyl; or groups such as benzhydryl, o-nitro-benzhydryl, acetonyl, trimethylsilyl, diphenyl-tert-butyl-silyl, and dimethyl-tert-butyl-silyl, or groups such as pivaloyloxy methyl or phthalidyl.

Particularly preferred carboxy protecting groups are allyl, p-nitrobenzyl, trimethylsilyl, dimethyl- tert-butyl-silyl, and trichloroethyl.

When in the compound of formula (III) R is a C$_1$-C$_3$ alkyl group substituted by hydroxy, the hydroxy is preferably protected, and a particularly preferred protecting group is dimethyl-tert-butyl-silyl.

The reaction between a compound of formula (II) and a compound of formula (III), may be performed in a suitable organic, preferably aprotic, solvent. Such a solvent may be, for instance, tetrahydrofuran, dimethylformamide, acetone or a halogenated hydrocarbon such as, e.g., dichloromethane.

The reaction temperature may, preferably, vary between about −100° C. and about +40° C., preferably between −70° C. and +15° C.

A compound of formula (III), wherein L is a sulphonyloxy group, may be prepared by reacting, according to known and conventional procedures, a carbinol precursor of formula (IV)

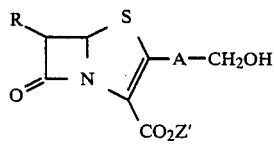

wherein R, A and Z' are as defined above, with the appropriate sulphonyl anhydride or sulphonyl halide, preferably triflic anhydride or triflic chloride, in the presence of a non-nucleophilic acid acceptor which may be, for instance, an inorganic base such as, e.g., calcium or lithium carbonate or calcium oxide, or an organic base such as, e.g., 2,6-lutidine, or also the same compound of formula (II) to be reacted in the subsequent step.

Indeed, according to a preferred procedure of the invention the compound of formula (IV) is made to react with the suitable sulphonyl anhydride or sulphonyl halide in the presence of an excess, usually an amount equal to or greater than 2 molar equivalents, of the desired compound of formula (II). In this situation the compound of formula (III) is not even isolated from the reaction mixture because it reacts in situ with the compound of formula (II). This preferred procedure is preferably carried out using dry dichloromethane as a solvent, at temperatures of from about −70° C. to +25° C.

When a compound of formula (II) is reacted with a compound of formula (III) wherein L is halogen, the presence of a silver salt, particularly if it is soluble in the media, e.g., AgClO$_4$, may be beneficial.

A compound of formula (III) wherein L is halogen, may be prepared from the corresponding carbinol precursor of formula (IV) according to a modified Mitsunobu reaction. Where this carbinol is allowed to react with an organic amine hydrohalide, such as, for instance, methoxyamine hydrochloride, pyridine hydrochloride, pyridine hydrobromide and the preformed complex obtained from diethylazodicarboxylate and triphenylphosphine. The reaction is carried out, e.g., in tetrahydrofuran or methylene chloride, preferably at a temperature around room temperature.

Alternatively, in the above modified Mitsunobu reaction a zinc halide, such as zinc chloride, zinc bromide or zinc iodide, can be substituted for the organic amine hydrohalide, under conditions substantially similar to those reported in *J. Org. Chem.*, 1984, 49, 3027.

Alternatively, a compound of formula (III) wherein L is halogen may be obtained from the carbinol of formula (IV) according to the more conventional procedures, entailing reaction with an inorganic acid halide such as SOCL$_2$, PCl$_5$, PCl$_3$, PBr$_3$, POCl$_3$, POBr$_3$ and the like.

An additional methodology well-known in the literature, namely the reaction with PPh$_3$ in CCl$_4$, can be exploited for the preparation of compounds of formula (III) where L is chloride. A compound of formula (III) where L is iodine can be prepared by a halide exchange reaction from a compound of formula (III) wherein L is chlorine or bromine and sodium iodide. This reaction is preferably carried out in acetone at temperatures ranging from 0° C. to +60° C. (reflux temperature). Some intermediates of formula (III), preferably when L is chloride, and the intermediates of formula (IV), either as such or as their protected derivatives, are known compounds or can be prepared from known compounds by following known general methodologies.

These include, for example:

(A) the thermal cyclization of a compound of formula (V)

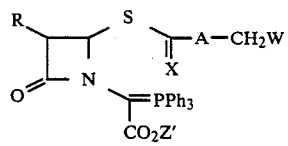

wherein R, A and Z' are as defined above, X represents sulphur or oxygen, and W is a free or a protected OH, or halogen, preferably chlorine, according to the method described, for example, in *J. Am. Chem. Soc.*, 1978, 100, 8214 and *Chem. Pharm. Bull.*, 1981, 29, 3158;

(B) the thermal cyclization of a compound of formula (VI)

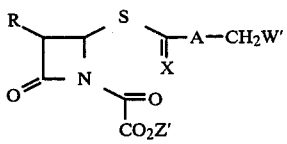

wherein R, X, A and Z' are as defined above, and W' is a free or a protected OH. The cyclization is performed in the presence of an organic phosphite, preferably trimethyl or triethyl phosphite, according to the method described, for example in *Chem. Pharm. Bull.*, 1983, 31, 768 and *Tetrahedron Lett.*, 1984, 25, 2395; or (C) the reaction of a compound of formula (VII)

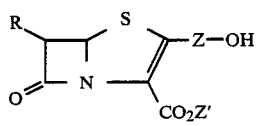

wherein R, X, Z and Z' are as defined above, with a carboxylic acid of formula (VIII), or an activated derivative thereof

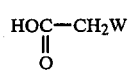

wherein W is as defined above, according to the method described, for example, in our British Patent Application No. 2,118,181—A— which is hereby incorporated by reference.

In particular, method C may be used to obtain intermediates of formula (III) and (Iv) wherein -A represents a group —Z—O—CO—. Method B may be used to obtain compounds of formula (IV). And method A may be used to obtain intermediates of the formula (III) or (IV).

Removal of the protecting groups can be effected by known per se procedures; e.g., silyl groups can be removed under mild acidic conditions, or by fluoride ions, e.g., with tetrabutylammonium fluoride; p-nitrobenzyl groups can be removed by reduction, e.g., by catalytic hydrogenation, or with metals, such as Fe and Zn; allyl carboxylates can be cleved by transallylation with an organic acid or a salt thereof, such as acetic acid, 2-ethylhexanoic acid or their sodium and potassium salts, this reaction being catalyzed by a triphenylphosphine-palladium complex, preferably by tetrakis-triphenyl-phosphine-Pd(o).

The optional salification of an obtained compound and the separation of a mixture of isomers into the single isomers may be carried out following known and conventional procedures.

Compounds of formula (II), (V), (VI), (VII), (VIII) are known compounds or can be prepared from known compounds according to known methods.

The compounds of formula (I) provided by the present invention are potent, broad spectrum antibacterial agents. In comparison to other penem compounds, e.g., the sodium salts derived from penems of formula (IV), or compounds of formula (I) wherein Q is an amine instead of quaternary ammonium, they usually show markedly increased in vitro activity against both Gram-positive and Gram-negative strains.

Moreover, in comparison with other penem compounds, they show unusually prolonged plasma levels. And when tested in vivo after parenteral administration, they displayed a very high degree of therapeutic effectiveness in treating infections caused by both Gram-positive and Gram-negative bacteria. Their toxicity, on the other hand, is quite negligible.

Table I shows the in vitro activity of a typical compound of formula (I), the compound 5 of the previous examples, in comparison with a classical penem of relevance, FCE 21420 (*J. Antibiotics*, 1982, 35, 1248) and the third generation cephalosporin Cefotaxime.

Table II shows "in vivo" the activity of compound 5.

TABLE I

In-Vitro Antibacterial Activity ($\gamma$/ml)
Against Gram-positive And Gram-negative bacteria
As Determined By The Agar Dilution Technique

| Organism | Compound 5[1] | FCE 21420[2] | Cefotaxime |
|---|---|---|---|
| *Staphylococcus aureus* Smith | 0.011 | 0.046 | 0.77 |
| *S. Aureus* 209 P | 0.005 | 0.046 | 1.56 |
| *S. Epidermidis* | 0.19 | 0.76 | 6.25 |
| *Streptococcus faecalis* (4 Strains) | 0.06 | 0.1 | 10 |
| *S. pyogenes* ATCC 12384 | 0.011 | 0.046 | 1.25 |
| *Klebsiella aerogenes* 1522 E | 0.38 | 1.55 | 0.095 |
| *K. aerogenes* 1082 E | 0.38 | 0.76 | 6.25 |
| *Escherichia coli* 026:B6 | 0.19 | 0.76 | 0.38 |
| *E. coli* 026:B6 cef R (IV) | 0.38 | 3.12 | 1.25 |
| *Proteus morganii* ATCC 25830 | 0.38 | 1.52 | 0.037 |
| *P. rettgeri* ATCC 9250 | 0.38 | 1.52 | 0.018 |
| *Citrobacter Freundii* ATCC 8090 | 0.19 | 1.52 | — |
| *Serratia marcescens* ATCC 2902 | 0.76 | 3.12 | — |

TABLE I-continued

In-Vitro Antibacterial Activity (γ/ml)
Against Gram-positive And Gram-negative bacteria
As Determined By The Agar Dilution Technique

| Organism | Compound 5[1] | FCE 21420[2] | Cefotaxime |
|---|---|---|---|
| *Pseudomonas aeruginosa* 2598 | 25 | 100 | 25 |

[1]Compound 5:

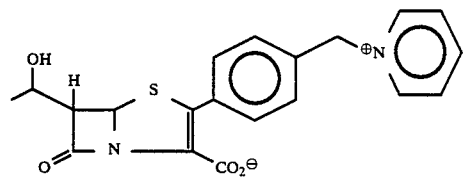

[2]FCE 21420:

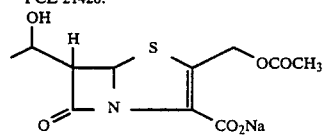

TABLE II

In-vivo data for "Compound 5"

| | t½ α | t½ β | (minutes) |
|---|---|---|---|
| Plasma half-life[1] | 5 | 15 | |

Experimental infections in mice[2]

| Strain | ED$_{50}$ (mg/kg, cumulative dose) |
|---|---|
| *Staphylococcus aureus* Smith | 0.06 |
| *Escherichia coli* G | 0.5 |
| *Klebsiella pneumoniae* FI 5724 | 0.8 |

[1]Determined after a single intravenous dose (10 mg/kg) in the mouse; the plasma concentration vs. time data were best described according to a two compartments open model with the tabulated t½
[2]Intraperitoneal infection in mice with a 3 × LD$_{50}$ challenge; treatments at 30 minutes after infection for *S. aureus* and 30, 90, 360 minutes for *E. coli* and *K. pneumoniae*.

Because of their high antibacterial activity, the compounds of the invention are useful, for example, in the treatment of respiratory tract infections, for example, bronchitis, bronchopneumonia or pleuritis; hepatobiliary and abdominal infections; septicemia; urinary tract infections, for example, pyelonephritis or cystitis; obstetrical and gynecological infections, for instance, cervicitis or endometritis; ear, nose and throat infections, for instance otitis, sinusitis or parotitis.

The compounds of the invention may be administered, either to humans or to animals, in a variety of dosage forms, e.g., orally in the form of tablets, capsules, drops or syrups; rectally in the form of suppositories; parenterally, e.g., intravenously or intramuscularly (as solutions or suspensions). Intravenous administration being preferred in emergency situations; by inhalation in the form of areosols or solutions for nebulizers; intravaginally in the form, e.g., of bougies; or topically in the form of lotions, creams and ointments. The pharmaceutical or veterinary compositions containing the compounds of formula (I), which are also within the scope of the invention, may be prepared in a conventional way by employing the conventional carriers or diluents used for e.g., cephalosporins.

Conventional carriers or diluents are, for example, water, gelatine, lactose, starches, magnesium stearate, talc, vegetable oils, cellulose and the like. Daily doses in the range of about 0.5 to about 100 mg per kg of body weight may be used, in various animal species. The exact dose depends on the age, weight and condition of the subject to be treated and on the frequency and route of administration.

A preferred way of administration of the compounds of the invention is parenteral administration. In this case the compounds may be administered, for example to adult humans, in an amount ranging from about 250 mg to about 1000 mg pro dose, preferably about 500 mg pro dose, 1-4 times a day, dissolved in a suitable solvent, such as, for example, sterile water of lidocaine hydrochloride solution for intramuscular injections, and sterile water, physiological saline solution, dextrose solution or the conventional intravenous fluids or electrolytes, for intravenous injections. Furthermore, the compounds of the invention may be used as antibacterial agents in a prophylactic manner, e.g., in cleaning or as surface disinfecting compositions, for example, at a concentration of about 0.2 to 1% by weight of such compounds admixed with, suspended, or dissolved in conventional inert dry or aqueous carriers for application by washing or spraying. They are also useful as nutritional supplements in animal feeds.

Other features of the invention will be apparent in the course of the following descriptions of exemplary embodiments which are given for illustration of the invention and are not intended to be limiting thereof.

EXAMPLE 1

(5R,6S)-6-[(1R)-hydroxyethyl]-2-[4-(N-methylpyrrolidiniomethyl) phenyl]-penem-3-carboxylate: (Compound 1)

A solution of (3S)-[(1R)-tertbutyldimethylsilyloxyethyl]-(4R)-[4-(tertbutyldiphenylsilyloxymethyl)-phenyl]acetyl-thio-1-[(α-triphenylphosphoranylidene)allyloxycarbonylmethyl]azetidin-2-one (1.6 g) in dry distilled tetrahydrofuran (16 ml) is treated with acetic acid (0.95 ml) and tetrabutylammonium fluoride trihydrate (1.25 g).

After 6 hours stirring at room temperature, the solvent was removed in vacuo and the residue was partitioned between diluted aq. NaHCO$_3$ and ethyl acetate.

The residue from the organic layer was purified by SiO$_2$ chromatography to afford (3S)-[(1R)-tertbutyldimethylsilyloxyethyl]-(4R)-[4-(hydroxymethyl)-phenyl]-acetylthio-1-[(α-triphenylphosphoranylidene)allyloxy-carbonylmethyl]azetidin-2one (1.0 g) as a foam.

A solution of this material in toluene (30 ml) was refluxed for 7 hours. The solvent was then removed and the residue passed through a SiO$_2$ column (EtOAc - cyclohexane as eluents). There was obtained allyl (5R, 6S)-6-[(1R)-tert-butyldimethyl-silyloxyethyl]-2-[4-(hydroxymethyl)phenyl]penem-3-carboxylate (375 mg) as a waxy solid: IR: $\nu$max (CH$_2$Cl$_2$) 1790, 1710 cm$^{-1}$; NMR (60 MHz, CDCl$_3$+D$_2$O): δ0.08 (6H, s, SiMe$_2$), 0.88 (9H, s, SiBu$^t$), 1.28 (3H, d, J=6 Hz, CH$_3$—CH), 3.68 (1H, dd, J=1.5 and 6 Hz, H-6), 4.2 (1H, m, CH$_3$CH), 4.5-4.7 (4H, m, ArCH$_2$+CO$_2$CH$_2$), 5.2 and 5.35 (2H, each m, =CH$_2$), 5.65 (1H, d, J=1.5 Hz, H-5), 5.9 (1H, m, CH$_2$CH=CH$_2$), 7-7.5 (4H, m, Ar) ppm.

A solution of the above intermediate (225 mg) in dry ethanol-free dichloromethane (10 ml), cooled at −50° C. under argon, was treated in sequence with N-methylpyrrolidine (0.25 ml) and trifluoromethanesulphonic anhydride (0.125 ml). The reaction mixture was warmed to −20° C. and after 20 minutes quenched with 0.1 M aqueous HCl. The organic layer was separated, washed with brine, dried and evaporated to give a residue which was triturated in ethyl acetate-ethyl ether mixtures, thus obtaining allyl (5R, 6S)-6-[(1R)-tert-butyldimethylsilyloxyethyl]-2-[4-(N-methylpyrrolidiniomethyl)phenyl]penem-3-carboxylate, as a powder (150 mg); IR: δmax (CHCl$_3$ film) 1785, 1710 cm$^{-1}$.

This material was taken up in tetrahydrofuran (9 ml) and acetic acid (0.18 ml), and tetrabutylammonium fluoride trihydrate (0.3 g) were added. The clear solution was let stand for 30 hours at room temperature, then concentrated and passed through a silica gel column packed with CH$_2$Cl$_2$.

The ammonium salts were eluted by a gradient of MeCN in CH$_2$Cl$_2$; then the product was eluted out by aqueous MeCN. The product-containing fractions were salted (NaCl) and the separated aqueous phase extracted twice with fresh MeCN. The MeCN phase and the MeCN extracts were collected, dried (MgSO$_4$) and evaporated to obtain salts (Cl$^-$, acetate) of allyl (5R,6S)-6[(1R)-hydroxyethyl]-2-[4-(N-methyl-N-pyrrolidioniomethyl)phenyl]penem-3-carboxylate (90 mg); IR: δmax (film) 3400-3200, 1785, 1710 cm$^{-1}$.

The above product (90 mg) in a 1:1 tetrahydrofuran-dichloromethane mixture (6 ml) was treated, in sequence, with acetic acid (0.03 ml), triphenylphosphine (9 mg) and tetrakis (triphenylphosphine) Pd(O) (9 mg).

After 10 minutes stirring, the addition of HOAc (acetic acid), PPh$_3$ and the catalyst was repeated and, after another 15 minutes, the solvents were removed in vacuo. The residue was dissolved in demineralized water and purified by reverse-phase chromatography (LiChroprep RP-18 Merck), eluting first with water, therewith a gradient in MeCN (from 95:5 to 1:1), and finally with H$_2$O-MeCN-EtOH (4:6:1). The appropriate fractions (TLC on SiO$_2$, i-PrOH/H$_2$O/HOAc 5:1:1, slow-running spot) were combined and freeze-dried to obtain 40 mg of the title product; IR: δmax (KBr) 3400, 1770, 1620 cm$^{-1}$; NMR (200 MHz, D$_2$O): δ1.31 (3H, d, J=6.3 Hz, CH$_3$CH), 2.23 (4H, m,

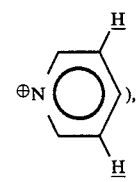

2.95 (3H, s, CH$_3$N$^+$), 3.3-3.7 (4H, m,

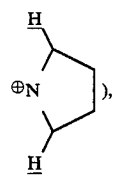

4.00 (1H, dd, J=1.6 and 6.0 Hz, H-6), 4.27 (1H, dq, J=6.0 and 6.3 Hz, CH$_3$—CH), 4.51 (2H, s, CH$_2$N$^+$), 5.80 (1H, d, J=1.6 Hz, H-5), 7.53 (4H, s, Ph) ppm; UV=λmax (H$_2$O): 250 and 330 nm.

EXAMPLE 2

(5R,6S)-6-[(1R)-hydroxyethyl]-2-[4-(pyridiniomethyl)phenyl]penem-3-carboxylate: (Compound 5)

A solution of allyl (5R,6S)-6-[(1R)-tertbutyldimethylsilyloxyethyl]-2-[4-(hydroxymethyl) phenyl]penem-3-carboxylate (300 mg) obtained as described in Example 1, in dry, ethanol-free dichloromethane (16 ml) was treated with pyridine (1.4 ml) and trifluoromethanesulphonic anhydride (0.8 ml) at −40° C. under nitrogen. After 30 minutes, 0.1M aqueous HCl (10 ml) was added, the organic layer was separated, washed with a further amount of 0.1N HCl, dried and evaporated.

The resulting residue (410 mg) was dissolved in tetrahydrofuran (20 ml) and stirred for 24 hours at room temperature in the presence of acetic acid (1 ml) and tetrabutylammonium fluoride trihydrate (1.6 g). Removal of the solvent and purification by silica gel chromatography (CH$_2$Cl$_2$, then CH$_2$Cl$_2$-MeCN, then MeCN-H$_2$O) afforded the allyl ester of the title compound (250 mg); IR: δmax (KBr) 3400, 1780, 1705 cm$^{-1}$; UV: λmax (EtOH) 256 and 336 um.

This material was dissolved in a 1:1 tetrahydrofuran-dichloromethane mixture and stirred under argon in the presence of acetic acid (0.25 ml), PPh$_3$ (25 mg) and tetrakis(triphenylphosphine) Pd(O) (25 mg).

More catalyst was added at ten minutes intervals (4×25 mg), until the reaction was judged complete by TLC (C$_6$H$_6$-EtOAc-HOAc-H$_2$O 9:9:15:5).

After evaporation in vacuo, the residue was dissolved in water and purified by reverse-phase chromatography.

Freeze-drying of the last eluted fractions afforded the title compound (100 mg); IR: δmax (KBr) 3400, 1770, 1600 cm$^{-1}$; NMR (200 MHz, D$_2$O): δ1.29 (3H, d, J=6.4 Hz, CH$_3$CH), 3.94 (1H, dd, J=1.6 and 6.0 Hz, H-6), 4.24 (1H, dq, J=6.0 and 6.4 Hz, CH$_3$CH), 5.74 (1H, d, J=1.6 Hz, H-5), 5.80 (2H, s, CH$_2$N$^+$), 7.43 (4H, m, Ph), 8.05 (2H, dd, J=6.5 and 7.7 Hz, 8.55 (1H, t, J=7.7 Hz,

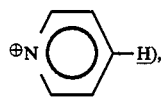

8.90 (2H, d, J=6.5 Hz,

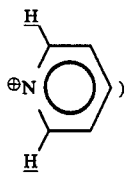

ppm; UV: λmax (H₂O): 254 and 330 nm.

EXAMPLE 3

(5R,6S)-6-[(1R)-hydroxyethyl]-2-[2-(pyridiniomethyl)phenyl]penem-3-carboxylate (Compound 14)

A mixture of potassium 2-hydroxymethylbenzoate (9.45 g) and chloroacetone (5 ml) in dry dimethylformamide (100 ml) was stirred for 3 hours at room temperature. Ethyl acetate and brine were then added and the organic layer, after further washing with water, was dried and evaporated to obtain acetonyl 2-hydroxymethylbenzoate (10 g) as a white powder. A solution of this material (1 g) in dimethylformamide (20 ml) was stirred for 3 hours in the presence of tert-butyldiphenylsilylchloride (2.32 ml) and imidazole (0.864 g).

The reaction mixture was partitioned between ethyl acetate and aqueous HCl; the dried organic phase was evaporated and the residue triturated in n-hexane to yield acetonyl 2-(tert-butyldiphenylsilyloxymethyl)benzoate (0.94 g) as a white solid; IR: δmax (CHCl₃) 740 sh, 1725 cm⁻¹; NMR (60 MHz, CDCl₃): δ1.15 (9H, s, SiBuᵗ), 2.15 (3H, s, CH₃), 4.70 (2H, s, CH₂CO), 5.20 (2H, s, PhCH₂O), 7.2-8.2 (14H, m, Ar) ppm. To this compound (0.78 g) dissolved in acetonitrile (25 ml), a solution of 0.1N NaOH was added (26.3 ml). The resulting mixture was concentrated in vacuo to half of its volume and ethyl acetate was added. The mixture was acidified with diluted HCl under stirring, the organic layer was separated, then washed twice with brine, dried and evaporated.

The solid residue was triturated in n-hexane and filtered thus obtaining 2-(tert-butyldiphenylsilyloxymethyl)-benzoic acid (0.54 g) as a white solid; m.p. 130°-132° C.

This product, dissolved in dry, ethanol-free dichloromethane (30 ml), was stirred for 6 hours at room temperature in the presence of thionyl chloride (0.5 ml). The reaction mixture was evaporated in vacuo from benzene (twice), thus obtaining 2-(tert-butyldiphenylsilyloxymethyl) benzoyl chloride, which was immediately used as such in the following step.

A solution of silver (3S)-[(1R)-tert-butyldimethylsilyloxyethyl]-1-[(α-triphenylphosphoranylidene) allyloxycarbonylmethyl]-2-oxoazetidinyl-4-thiolate (0.7 g) in dry dichloromethane (25 ml) was allowed to react with the above acyl chloride (0.55 g) and pyridine (0.08 ml) for 30 minutes at room temperature. After addition of Celite and charcoal, the mixture was stirred for a further 10 minutes, filtered through Celite and sequentially washed with 4% aq. HCl, brine, aq. NaHCO₃. Flash-chromatography afforded (3S)-[(1R)-tert-butyldimethylsilyloxyethyl] (4R)-[2-(tert-butyldiphenylsilyloxymethyl)phenyl]acetylthio-1-[α-triphenylphosphoranylidene)allyloxycarbonylmethyl]azetidin-2-one (0.8 g) as a foam; IR: δmax (CHCl₃) 1740, 1660, 1610 cm⁻¹.

This intermediate was dissolved in dry xylene and refluxed for 7 hours in the presence of a catalytic amount of hydroquinone (20 mg). The cooled reaction mixture was passed through a SiO₂ column, thereby obtaining allyl (5R,6S)-6-[(1R)-tert-butyldimethylsilyloxyethyl]-2-[2-(tert-butyldiphenylsilyloxymethyl)phenyl]penem-3-carboxylate (0.4 g); IR: δmax (film) 1790, 1710 cm⁻¹; NMR (60 MHz, CDCl₃): δ0.06 (6H, s, SiMe₂), 0.8 (9H, s, SiBuᵗ), 1.1 (9H, s, SiBuᵗ), 1.25 (3H, d, J=6.5 Hz, CH₃CH), 3.6 (1H, dd, J=1.5 and 4.5 Hz, H-6), 4.3 (1H, m, CH₃CH), 4.5 (2H, d, CH₂CH=CH₂), 4.7 (2H, s, ArCH₂O), 4.9 (2H, m, CH=CH₂), 5.5 (1H, d, J=1.5 Hz, H-6), 5.7 (1H, m, CH₂—CH=CH₂), 7.1-7.7 (14H, m, Ar) ppm.

To a solution of this material (400 mg) in dry tetrahydrofuran (20 ml), acetic acid (0.7 ml) and tetrabutylammonium fluoride trihydrate (500 mg) were added. The mixture was stirred for 5 hours, the solvent was removed in vacuo and the residue purified by flash-chromatography (EtOAc-cyclohexane mixtures) to obtain allyl (5R,6S)-6-[(1R)-tert-butyldimethylsilyloxyethyl]-2-[2-(hydroxymethyl)phenyl]penem-3-carboxylate as a white foam (250 mg); IR: δmax (film) 3400, 1790, 1705 cm⁻¹; NMR (60 MHz, CDCl₃): δ0.05 (6H, s, SiMe₂), 0.9 (9H, s, SiBuᵗ), 1.25 (3H, d, CH₃CH), 2.3 (1H, br s, OH), 3.8 (1H, dd, J=1.8 and 5 Hz, H-6), 4.3 (1H, m, CH₃CH), 4.52 (2H, d, J=5 Hz, CH₂CH=CH₂), 4.65 (2H, s, ArCH₂), 5.2 (2H, m, CH₂=CH₂), 5.5-5.9 (1H, m, CH₂—CH—CH₂), 5.85 (1H, d, J=1.8 Hz, H-5), 7.2-7.8 (4H, m, Ar) ppm.

Pyridine (0.1 ml) and trifluoromethanesulphonic anhydride (0.1 ml) were added to a solution of the above intermediate (100 mg) in dry CH₂Cl₂ (2 ml) at −60° C. under nitrogen. After 15 minutes stirring at −40° C., the reaction mixture as quenched with 4% HCl and brine.

The organic layer was separated, washed twice with brine and evaporated to leave a residue which was triturated with ethyl ether, thus obtaining allyl (5R,6S)-6-[(1R)-tert-butyldimethylsilyloxyethyl]-2-[2-(pyridiniomethyl)phenyl]penem-3-carboxylate, chloride salt, as a white crystalline solid; IR: νmax (KBr) 1795, 1705 cm⁻¹; NMR (200 MHz, acetone d₆, 45° C.): δ0.11 (6H, s, SiMe₂), 0.91 (9H, s, SiBuᵗ), 1.28 (3H, d, J=6.4 Hz, CH₃CH), 4.07 (1H, m, H-6), 4.3-4.4 (3H, m, OCH₂-CH—CH₂ and CH₃CH), 5.10 and 5.18 (each 1H, m, CH=CH₂), 5.68 (1H, m, CH₂CH=CH₂), 5.95 (1H, d, J=1.7 Hz, H-5), 6.10 (2H, m, PhCH₂N⁺), 7.4-7.8 (4H, m, Ph), 8.19 (2H, dd, J=5.7 and 7.8 Hz).

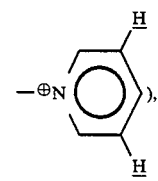

8.72 (1H, t, J=7.8 Hz,

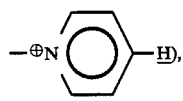

and 9.05 (2H, d, J=5.7 Hz,

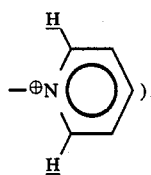

ppm.

Sequential treatment of this product with tetrabutylammonium fluoride and finally with HOAc/PPh₃/(PPh₃)₄Pd under the identical conditions indicated in Example 2 afforded a sample (25 mg) of the title compound; IR: δmax (KBr) 3400, 1765, 1590 cm⁻¹; UV: λmax (H₂O) 330 nm.

EXAMPLE 4

Operating as described in the previous examples, the following compounds were analogously prepared:

(5R,6S)-6-[(1R)-hydroxyethyl]-2-[4-(N-methylpiperidiniomethyl)phenyl]penem-3-carboxylate (2);

(5R,6S)-6-[(1R)-hydroxyethyl]-2-[4-(N,N,N-trimethylammoniomethyl)phenyl]-3-carboxylate (3);

(5R,6S)-6-[(1R)-hydroxyethyl]-2-[4-(N,N,N-triethylammoniomethyl)-phenyl]penem-3-carboxylate (4);

(5R,6S)-6[(1R)hydroxyethyl]-2-{4-[6,7-dihydro-5H-cyclopenta-[b]-pyridinio)methyl]phenyl}penem-3-carboxylate (6);

(5R,6S)-6-[(1R)-hydroxyethyl[-2-{4-[(4-carbamoylpyridinio)methyl[phenyl}penem-3-carboxylate (7);

(5R,6S)-6-[(1R)-hydroxyethyl]-2-{4-[(5-ethyl-2-methylpyridinio)methyl]phenyl}penem-3-carboxylate (8);

(5R,6S)-6-hydroxyethyl]-2-[4-(quinoliniomethyl) phenyl]penem-3-carboxylate (9);

(5R,6S)-[(1R)-hydroxyethyl]-2-[4-(quinuclidiniomethyl)phenyl]penem-3-carboxylate (10);

(5R,6S)-6- [(1R)-hydroxyethyl]-2-{4-[(1-methylomorpholinio)methyl]phenyl}penem-3-carboxylate (11);

(5R,6S)-6-[(1R)-hydroxyethyl]-2-{4-[(1-methylpiperazinio)methyl]phenyl}penem-3-carboxylate (12);

(5R,6S)-6-[(1R)-hydroxyethyl]-2-{4-[(1,4-dimethylpiperazino)methyl]phenyl}penem-3-carboxylate (13);

(5R,6S)-6-[(1R)-hydroxyethyl]-2-[2-(isoquinuclidiniomethyl)phenyl]penem-3-carboxylate (15);

(5R,6S)-6-[(1R)-hydroxyethyl]-2-{2-[(3-cyanomethylpyridinio)methyl]phenyl}penem-3-carboxylate (16);

(5R,6S)-6-[(1R)-hydroxyethyl]-2-2-[2-(pyraziniomethyl) phenyl]penem-3-carboxylate (17);

(5R,6S)-6-[(1R)-hydroxyethyl]-2-[2-(N,N,N-trimethylammoniomethyl)phenyl]penem-3-carboxylate (18);

(5R,6S)-6-[(1R)-hydroxyethyl]-2-[2-(N,N,N-triethylammoniomethyl)phenyl]phnem-3-carboxylate (19);

(5R,6S)-6-[(1R)-hydroxyethyl]-2-[2-(N-methylidiniomethyl)phenyl]penem-3-carboxylate (20);

(5R,6S)-6-(1R)-hydroxyethyl]-2-[2-(N-methylpiperidiniomethyl)phenyl]penem-3-carboxylate (21);

(5R,6S)-6-[(1R)-hydroxyethyl]-2-[3-(pyridiniomethyl)phenyl]penem-3-carboxylate (22);

(5R,6S)-6-[(1R)-hydroxyethyl]-2-[3-(N-methylpyrrolidiniomethyl)phenyl]penem-3-carboxylate (23);

(5R,6S)-6-[(1R)-hydroxyethyl]-2-[3-(N,N,N-trimethylammoniomethyl)phenyl]penem-3-carboxylate (24);

(5R,6S)-6-[(1R)-hydroxyethyl]-2-[(E)-2-(pyridiniomethyl)ethenyl]penem-3-carboxylate (38);

(5R,6S)-6-[(1R)-hydroxyethyl]-2-[(Z)-2-(pyridiniomethyl)ethenyl]penem-3-carboxylate (39);

(5R,6S)-6-[(1R)-hydroxyethyl]-2-[(Z)-2-(N-methylpyrrolidiniomethyl)phenyl]penem-3-carboxylate (40);

(5R,6S)-6-[(1R)-hydroxyethyl]-2-[5-(N-methylpyrrolidiniomethyl)thien-2-yl]penem-3-carboxylate (28);

(5R,6S)-6-[(1R)-hydroxyethyl]-2-[4-(pyridinioacetyl) phenyl]penem-3-carboxylate (44);

(5R,6S)-6-[(1R)-hydroxyethyl]-2-[3-(pyridinioacetyl) phenyl]penem-3-carboxylate (45);

(5R,6S)-6-[(1R)-hydroxyethyl]-2-[4-(2-oxo-3-pyridiniopropyl)phenyl]penem-3-carboxylate (46);

(5R,6S)-6-[(1R)-hydroxyethyl]-2-{4-[(3-methylthiopyridinio)methyl]phenyl}penem-3-carboxylate (47);

(5R,6S)-6-[(1R)-hydroxyethyl]-2-{3-[(4-methylthiopyridinio)methyl]phenyl}penem-3-carboxylate (48); and (5R,6S)-6-[(1R)-hydroxyethyl]-2-{3-[(4-methoxypyridinio)methyl]phenyl}penem-3-carboxylate (49).

EXAMPLE 5

(5R,6S)-6-[(1R)-hydroxyethyl]-2-[(N-methylpyrrolidinio)acetoxymethyl]penem-3-carboxylate (Compound 41)

A solution of allyl (5R,6S)-6-[(1R)-tertbutyldimethylsilyloxyethyl]-2-(hydroxymethyl)penem-3carboxylate (480 mg) in dry dichloromethane (15 ml) was sequentially treated with triphenylphosphine (790 mg), tert-butyldiphenylsilyloxyacetic acid (420 mg) and diethyl azodicarboxylate (0.475 ml). A mild exothermic reaction took place and rapidly subsided The solvent was removed and the residue was purified by silica gel chromatography, thus obtaining allyl(5R,6S)-6-[(1R)-tertbutyldimethylsilyloxyethyl]-2-[(tertbutyldiphenylsilyloxy)acetoxymethyl]penem-3-carboxylate (700 mg), IR: νmax (CHCl₃) 1780, 1740, 1710 cm⁻¹.

This material was dissolved in a tetrahydrofuran solution (30 ml) of tetrabutylammonium fluoride trihydrate (630 mg) and acetic acid (0.92 ml). After 1 hour standing at room temperature, the solvent was removed and the residue purified by silica gel chromatography to obtain allyl (5R,6S)-6-[(1R)-tertbutyldimethylsilyloxyethyl]-2-[(hydroxymethyl)acetoxymethyl]penem-3-carboxylate as a yellowish oil (250 mg); IR: δmax (CHCl₃) 1785, 1745, 1705 cm⁻¹; NMR (60 MHz, CDCl₃): δ0.1 (6H, s, SiMe₂), 0.9 (9H, s, SiBuⁱ), 1.25 (3H, d, J=6 Hz, CH₃CH), 3.70 (1H, dd, J=1.5 and 4.5 Hz, H-6), 4.2 (3H, m, COCH₂O+CH₃CH), 4.75 (2H, m, CO₂CH₂), 5.2 and 5.4 (2H, each m, =CH₂), 5.35 (2H, ABq, J=15 Hz, 2—CH₂O), 5.6 (1H, d, J=1.5 Hz, H-5), 5.8–6.2 (1H, m, CH=CH₂) ppm. The above intermediate (200 mg) was dissolved in dry CH₂Cl₂ (10 ml) and the cooled solution (−70° C., nitrogen atmosphere) was treated in sequence with N-methylpyrrolidine (0.22 ml) and trifluoromethanesulphonic anhydride (0.17 ml). After 10 minutes, the reaction mixture was diluted with more CH₂Cl₂, washed with 4% aq. HCl, then with water, dried and evaporated.

The oily residue was stirred for 20 hours in a tetrahydrofuran solution (8 ml) containing acetic acid (0.5 ml) and tetrabutylammonium fluoride trihydrate (470 mg).

The solvent was then removed and the residue loaded on a SiO$_2$ column packed in dichloromethane. Sequential elution with CH$_2$Cl$_2$, CH$_2$Cl$_2$-EtOH (1:1), EtOH-MeCN gave some impurities, while the desired salts of allyl (5R,6S)-6-[(1R)-hydroxyethyl]-2[(N-methylpyrrolidinio)acetoxymethyl]penem-3-carboxylate were collected by eluting with 35° aq. MeCN.

The product-containing fractions were collected, saturated with NaCl and extracted with MeCN.

The organic extracts were dried and evaporated; the residue was taken up in dry CH$_2$Cl$_2$ (10 ml) containing HOAc (0.2 ml), and triphenylphosphine (50 mg) followed by tetrakis(triphenylphosphine) Pd(O) (40 mg) were added.

After 30 minutes stirring a room temperature, the catalyst was filtered off and after removal of the solvent, the crude product was dissolved in water and purified by reverse-phase chromatography (LiChroprop RP-18 Merck, water).

The title product was eluted out with H$_2$O-MeCN and freeze-dried; white powder, 40 mg; IR: δmax (KBr) 3400, 1765, 1610 cm$^{-1}$; UV: νmax (H$_2$O) 258 and 308 nm; NMR (200 MHz, D$_2$O): δ1.29 (3H, d, J=6.4 Hz, CH$_3$CH), 2.24 (4H, m,

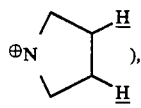), 3.27 (3H, s, $^+$NCH$_3$), 3.6–3.9 (4H, m,

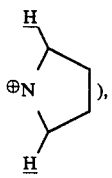), 3.93 (1H, dd, J=1.4 and 5.9 Hz, H-6), 4.24 (1H, dg, J=5.9 and 6.4 Hz, CH$_3$—CH), 4.45 (2H, s, CH$_2$N+), 5.22 and 5.63 (2H, ABq, J=14.0 Hz, 2—CH$_2$), 5.68 (1H, d, J=1.4 Hz, H-5) ppm.

EXAMPLE 6

Operating as described in the former example, there were obtained:
(5R,6S)-6-[(1R)-hydroxyethyl]-2-[2-(pyridinioacetoxy)ethyl]penem-3-carboxylate (42); and
(5R,6S)-6-[(1R)-hydroxyethyl]-2-{2-[(N-methylpyrrolidinio)acetoxy]ethyl}penem-3-carboxylate (43).

EXAMPLE 7

(5R,6S)-6-[(1R)-hydroxyethyl]-2-[3-(N-methylpyrrolidinio)propyl]penem-3-carboxylate (Compound 31)

PROCEDURE A—To a solution of allyl (5R,6S)-6-[(1R)-tert-butyldimethylsilyloxyethyl]-2-(3-hydroxypropyl)penem-3-carboxylate (400 mg) in dry ethanol-free dichloromethane (15 ml, cooled at −30° C. under nitrogen, N-methylpyrrolidine (0.47 ml) and trifluoromethanesulphonic anhydride (0.36 ml) were added in sequence.

The bath was removed and the reaction mixture was kept at room temperature until most of the starting material had disappeared (TLC monitoring). More dichloromethane and 0.1M aqueous HCl were added under stirring and the separated organic phase was washed with brine, dried and evaporated to afford an oily residue, mainly consisting of salts (chloride, triflate) of allyl (5R,6S)-6-[(1R)-tert-butyldimethylsilyloxyethyl]-2-[3-(N-methylpyrrolidinio)propyl]penem-3-carboxylate.

Without purification, this material was added to a solution of tetrabutylammonium fluoride trihydrate (1.8 g) in tetrahydrofuran (15 ml) and acetic acid (1 ml), and the desilylation monitored by TLC. When the reaction was completed, the solvent was removed in vacuo and the residue was purified by flash-chromatography (CHCl$_2$-MeCN and then MeCN-H$_2$O).

The obtained product (0.27 g), the allyl ester of the title compound, was stirred for 30 minutes under nitrogen in a mixture of triphenylphosphine (50 mg) and tetrakis(triphenylphosphine) palladium (50 mg) in dichloromethane-tetrahydrofuran (7 ml+7 ml) and acetic acid (0.5 ml).

The catalyst was filtered off and the solution, after removal of the solvent, was passed through a column packed with LiChroprep RP-18 Merck by eluting with water and then with 10% MeCN in H$_2$O. Freeze-drying of the relevant fractions afforded the title product (70 mg); IR: νmax (KBr) 3400, 1765, 1605 cm$^{-1}$; UV: λmax (H$_2$O) 304 nm.

PROCEDURE B—Allyl (5R,6S)-6-[(1R)-tertbutyldimethylsilyloxyethyl]-2-(3-chloropropyl)penem-3carboxylate (270 mg) and sodium iodide were refluxed under argon in dry acetone until the reaction was judged complete by TLC. Most of the solvent was then removed in vacuo and the residue was partitioned between ethyl acetate and water.

The dried organic layer was concentrated to give a residue which was purified by short-path flash-chromatography, thereby obtaining allyl (5R,6S)-6-[(1R)-tert-butyldimethylsilyloxyethyl]-2-(3-iodopropyl)penem-3-carboxylate as a syrup (220 mg); IR: νmax (film) 1790, 1710 and 1580 cm$^{-1}$.

To a solution of the above material in dry tetrahydrofuran (30 ml), N-methylpyrrolidine (0.1 ml) and silver perchlorate (165 mg) were added. The reaction mixture was stirred for 6 hours at 0° C. and then warmed to room temperature in a nitrogen atmosphere in the dark. The solvent was removed and the residue was partitioned between dichloromethane and 0.1N HCl at 5° C. The organic layer was collected, filtered and evaporated to leave a residue consisting of salts (mainly chloride) of allyl (5R,6S)-6-[(1R)-tert-butyldimethylsilyloxyethyl]-2-[3-(N-methylpyrrolidinio)propyl]penem-3-carboxylate. This intermediate was processed through the desilylation and deallylation steps as described above under Procedure A, thus obtaining an identical sample of the title compound.

EXAMPLE 8

By following the protocol described in the previous example,
(5R,6S)-6-[(1R)-hydroxyethyl]-2-[1-(pyridiniomethyl)cyclopentyl]penem-3-carboxylate (25);
(5R,6S)-6-[(1R)-hydroxyethyl]-2-[1-(N-methylpyrrolidiniomethyl)cyclopentyl]penem-3-carboxylate (26);

(5R,6S)-6-[(1R)-hydroxyethyl]-2-[1-(N,N,N-triethylammoniomethyl)cyclopentyl]penem-3-carboxylate (27);

(5R,6S)-6-[(1R)-hydroxyethyl]-2-[3-(N,N,N-trimethylammoniomethyl)cyclobutyl]penem-3-carboxylate (36);

(5R,6S)-6-[(1R)-hydroxyethyl]-2-[3-(pyridiniomethyl)cyclopentyl]penem-3-carboxylate (37);

(5R,6S)-6-[(1R)-hydroxyethyl]-2-(3-pyridiniopropyl)penem-3-carboxylate (29);

(5R,6S)-6-[(1R)-hydroxyethyl]-2-[3-(3-cyanomethylpyridinio)propyl]penem-3-carboxylate (30);

(5R,6S)-6-[(1R)-hydroxyethyl]-2-[3-(N,N,N-trimethylammonio)propyl]penem-3-carboxylate (32);

(5R,6S)-6-[(1R)-hydroxyethyl]-2-[4-(3-cyanomethylpyridinio)butyl]penem-3-carboxylate (33);

(5R,6S)-6-[(1R)-hydroxyethyl]-2-(4-pyridiniobutyl)penem-3-carboxylate (34); and (5R,6S)-6-[(1R)-hydroxyethyl]-2-[4-(N-methylpyrrolidinio)butyl]penem-3-carboxylate (35) were obtained.

EXAMPLE 9

(5R,6S)-6-[(1R)-hydroxyethyl]-2-{4-[(3,5-dimethylpyridinio)methyl]phenyl}penem-3-carboxylate (Compound 54)

Operating as in Example 2, but employing 3,5-dimethylpyridine instead of pyridine, the title compound was obtained (700 mg); UV (H$_2$O): λmax 328, 268 nm; NMR (200 MHz, D$_2$O): δppm 1.30 (3H, d, J=6.2 Hz), 2.47 (6H, s), 3.93 (1H, d, J=1.6 and 5.8 Hz), 4.25 (1H, dq, J=5.8 and 6.2 Hz), 5.68 (2H, s), 5.73 (1H, d, J=1.6 Hz), 7.3–7.4 (4H, m), 8.19 (1H, m), 8.55 (2H, m).

EXAMPLE 10

(5R,6S)-6-[(1R)-tert-butyldimethylsilyloxyethyl]-2[4-(bromomethyl)phenyl]penem-3-carboxylate Step (A)—A solution of (3S)-[(1R)-tertbutyldimethylsilyloxyethyl]-(4R)-triphenylmethylthio-1-(1-allyloxycarbonyl-1-triphenylphosphoranylidenemethyl)azetidin-2-one (5 g) and imidazole (0.75 g) in methanol (15 ml) was added to a stirred suspension of powdered silver nitrate (1.97 g) in the same solvent (20 ml) under nitrogen and in the dark. After 15 minutes, dichloromethane (250 ml) was added; the organic layer was washed with water (2×200 ml), dried (Na$_2$SO$_4$) and evaporated to give 4.7 g of crude silver (3S)-[(1R)-tert-butyldimethylsilyloxyethyl]-1-(1-allyloxycarbonyl-1-triphenylphosphoranylidenemethyl)-2-oxoazetidinyl-4-thiolate as a brown foam.

Step (B)—A solution of α-bromotoluic acid (1.08 g) in dry benzene (10 ml) was stirred for 2 hours with thionyl chloride (0.73 ml) and dry DMF (five drops). The reaction mixture was evaporated to dryness, taken up in toluene and evaporated again. The crude product was crystallized from n-hexane (10 ml, charcoal) thereby obtaining pure α-bromotoluic acid chloride (0.95 g) as white flakes.

This product was added to a solution of the silver thiolate from the step (A) above (2.2 g) in dry dichloromethane. After 25 minutes stirring, the precipitated AgCl was filtered off and the organic solution was washed with brine and with aqueous NaHCO$_3$.

The residue resulting from removal of the solvent was purified by SiO$_2$ chromatography, thereby obtaining (3S)-[(1R)-tert-butyldimethylsilyloxyethyl]-(4R)-[4-(bromomethyl)phenyl]thio-1-(1-allyloxycarbonyl-1-triphenylphosphoranylidenemethyl)azetidin-2-one (2 g) as a foam; IR (CHCl$_3$): νmax 1750, 1660, 1605 cm$^{-1}$.

Step (C)—The product from step (B) above was dissolved in dry toluene and heated in an oil bath (100° C.) for 12 hours under nitrogen and in the presence of a catalytic amount of hydroquinone. Silica gel chromatography (cyclohexane-ethyl acetate) afforded the title product (1.3 g) as white flakes; IR (CHCl$_3$): νmax 1785, 1705 cm$^{-1}$; NMR (90 MHz, CDCl$_3$) δppm 0.05 and 0.12 (each 3H, s), 0.82 (9H, s), 1.20 (3H, d, J=6.5 Hz), 3.66 (1H, dd, J=1.5 and 4.5 Hz), 4.2 (1H, m), 4.35 (2H, s), 4.45 (2H, m), 5.0–5.2 (2H, m), 5.60 (1H, d, J=1.5 Hz), 5.5–5.9 (1H, m), 7.35 (4H, m).

EXAMPLE 11

Allyl (5R,6S)-6-[(1R)-hydroxyethyl]-2-[4-(bromomethyl)phenyl]penem-3-carboxylate Step (A)—Aqueous 2N HCl (80.3 ml) was added to a solution of (3S)-[(1R)-tert-butyldimethylsilyloxyethyl]-(4R)-triphenylmethylthio-1-(1-allyloxycarbonyl-1-triphenylphosphoranylidenemethyl)azetidin-2-one (34.62 g) in THF (346 ml).

After standing overnight, most of the solvent was removed in vacuo and the resulting mixture was partitioned between EtOAc and brine. The organic layer was washed twice with aq. NaHCO$_3$, dried and evaporated, thereby obtaining crude (3S)-[(1R)-hydroxyethyl]-(4R)-triphenylmethylthio-1-(1-allyloxycarbonyl-1-triphenylphosphoranylidenemethyl)azetidin-2-one as a foam in quantitative yield.

Step (B)—A saturated solution of AgNO$_3$ (8.5 g) in methanol (333 ml) under nitrogen and in the dark was treated at 20° C. with a solution of the material of step (A) above and imidazole (2.7 g) in methanol (100 ml). After 5 minutes, most of the solvent was removed in vacuo and the residue was taken up in EtOAc. The organic layer was washed with water (3×), dried (MgSO$_4$), concentrated to 150 ml and treated under stirring with ethyl ether (300 ml). After further 10 minutes stirring, the precipitated silver (3S)-[(1R)hydroxyethyl]-1-(1-allyloxycarbonyl-1-triphenylphosphoranylidenemethyl)-2-oxoazetidinyl-4thiolate was collected as a white powder in quantitative yield (24.5 g); IR (CHCl$_3$): δmax 1740, 1615 cm$^{-1}$.

Step (C)—The material from step (B) above (24 g) was reacted with α-bromotoluic acid chloride (11.7 g) as described in Example 10, Step (B).

Work-up and chromatography afforded (3S)-[(1R)hydroxyethyl]-(4R)-[4-(bromoethyl)phenyl]thio-1(1-allyloxycarbonyl-1-triphenylphosphoranylidenemethyl)-azetidin-2-one (20.6 g) as a foam; IR (CHCl$_3$): νmax 1750, 1660, 1605 cm$^{-1}$.

Step (D)—The material from step (C) above was heated for 10 hours in a toluene solution at 90° C. under nitrogen and in the presence of hydroquinone.

Silica gel chromatography afforded first some allyl 5-[4-(bromomethyl)phenyl]-1,3-thiazole-4-carboxylate, and then the title product (8.65 g), as white needles (from ethyl ether); m.p. 121°–122° C.

NMR (200 MHz, CDCl$_3$): δppm 1.36 (3H, d, J=6.3 Hz), 3.81 (1H, dd, J=1.5 and 6.6 Hz), 4.27 (1H, dq, J=6.3 and 6.6 Hz), 4.47 (2H, s), 4.57 (2H, m), 5.14 (1H, d, J=10.0 Hz), 5.15 (1H, d, J=17.0 Hz), 5.7–5.9 (1H, m), 5.71 (1H, d, J=1.5 Hz), 7.4–7.5 (4H, m).

EXAMPLE 12

(5R,6S)-6-[(1R)-hydroxyethyl]-2-{4-[(3-hydroxypyridinio)methyl]phenyl}penem-3-carboxylate (Compound 55)

A mixture of allyl (5R,6S)-6-[(1R)-tert-butyldimethylsilyloxyethyl]-2-[4-(bromomethyl)phenyl]penem-3-carboxylate (110 mg) and 3-(tert-butyldimethylsilyloxy)pyridine (125 mg) in DMF (2 ml) was stirred overnight at room temperature.

The solvent was then evaporated in vacuo, ether was added and the suspension was stirred for 1 hour at room temperature.

The yellowish solid was then collected yielding 100 mg of allyl (5R,6S)-6-[(1R)-tert-butyldimethylsilyloxyethyl]-2-{4-[3-hydroxypyridinio)methyl]phenyl}penem-3-carboxylate, bromide salt; NMR (90 MHz, CDCl$_3$): δppm 0.12 (6H, s), 0.82 (9H, s), 1.20 (3H, d, J=6.0 Hz), 3.70 (1H, dd, J=1.6 and 5.0 Hz), 4.18 (1H, dd, J=5.0 and 6.0 Hz), 4.45 (2H, m), 5.02 (1H, d, J=10.0 Hz), 5.14 (1H, d, J=17.0 Hz), 5.61 (1H, d, J=1.6 Hz), 5.5–5.7 (1H, m), 5.82 (2H, s), 7.50 (4H, s), 7.4–7.7 (1H, m), 7.8–8.0 (1H, m), 8.2–8.4 (1H, m), 8.68 (1H, m), 9.26 (1H, br s).

This compound was dissolved in dry TMF and stirred overnight in the presence of acetic acid (100 ml) and tetrabutylammonium fluoride trihydrate (125 mg).

The reaction mixture was then evaporated in vacuo and partially purified on silica gel eluting with acetonitrile/water mixtures. The resulting solution was then evaporated in vacuo to yield allyl (5R,6S)-6-[(1R)-hydroxyethyl]-2-4-[(3-hydroxypyridinio)methyl]phenyl penem-3-carboxylate, bromide salt, as a yellow oil (80 mg).

This product was then dissolved in THF/CH$_2$Cl$_2$.

Acetic acid (0.8 ml), triphenylphosphine (80 mg) and (Ph$_3$P)$_4$Pd (30 mg) were then sequentially added.

The reaction, performed as indicated in previous examples, afforded 20 mg of the title compound; IR: νmax (KBr) 3400, 1770, 1600 cm$^{-1}$ UV: λmax (H$_2$O) 326, 250 nm.

EXAMPLE 13

(5R,6S)-6-[(1R)-hydroxyethyl]-2-{4-[(4-ethansulfonate-1-pyridinio)methyl]phenyl penem-3carboxylic acid (compound 55/a)

A mixture of allyl (5R,6S)-6-[(1R)hydroxyethyl]-2-[4-(bromomethyl)phenyl]penem-3-carboxylate (100 mg) and sodium 4-pyridine-ethanesulfonate (145 mg) in dry DMF was stirred for 48 hours at room temperature.

The mixture was then evaporated in vacuo and the residue purified by reverse phase chromatography to yield, after freeze-drying, 40 mg of allyl (5R,6S)-6-[(1R)-hydroxyethyl]-2-{4-[(4-ethanesulfonate-1-pyridinio)methyl]phenyl}penem-3-carboxylate.

IR (KBr): 3400, 1790, 1710 cm$^{-1}$.

UV (H$_2$O/10% CH$_3$CN): 335 nm.

NMR (200 MHz, D$_2$O): δppm 1.30 (3H, d, J=6.4 Hz), 3.34 (4H, m), 4.05 (1H, dd, J=1.5 and 5.6 Hz), 4.26 (1H, dq, J=5.6 and 6.4 Hz), 5.04 (1H, d, J=16.2 Hz), 5.6–5.8 (1H, m), 5.78 (2H, s), 5.80 (1H, d, J=1.5 Hz), 7.46–7.54 (4H, ABq, J=8.4 Hz), 7.98 (2H, d, J=6.7 Hz), 8.77 (2H, d, J=6.7 Hz).

Treatment of this product with HOAc/Ph$_3$P/(Ph$_3$P)$_4$Pd under the identical conditions indicated in Example 2 afforded a sample (20 mg) of the title compound.

IR (KBr): 3400, 1775, 1700 cm$^{-1}$.

UV (H$_2$O): 330, 252 nm.

NMR (200 MHz, D$_2$O, t=45° C.): δppm 1.56 (3H, d, J=6.5 Hz), 3.60 (4H, m), 4.27 (1H, dd, J=1.5 and 5.8 Hz), 4.51 (1H, dq, J=5.8 and 6.5 Hz), 6.02 (2H, s), 6.05 (1H, d, J=1.5 Hz), 7.69–7.79 (4H, ABq, J=8.3 Hz), 8.24 (2H, d, J=6.8 Hz), 9.00 (2H, d, J=6.8 Hz).

EXAMPLE 14

By following the experimental procedure described in the above Example 13 and replacing sodium 4-pyridineethansulphonate with 3-hydroxymethylpyridine, 2-(2-hydroxyethly)pyridine, 8-hydroxyquinoline, 8-hydroxyisoquinoline, 3-formylaminopyridine, isonicotinohydroxamic acid, 3-pyridinecarboxaldehyde, 3-pyridinealdoxime, 4-acetylpyridine oxime, 3-aminopyridine, pyrazine, 1-methyl-1,2,3-triazole, 1-methylpyrazole, thieno[2,3-c]pyridine, furo[2,3c]pyridine, furo [3,2-c]pyridine, thieno[3,2c]pyridine, thieno[2,3-b]pyridine, furo[2,3-b]pyridine, thieno[3,4-c]pyridine, and thiazolo[4,5-c]pyridine, there were obtained, respectively, (5R,6S)-6-[(1R)-hydroxyethyl]-2-{4-[(3-hydroxymethyl-1pyridinio)methyl]phenyl}penem-3-carboxylate (Compound 56);

(5R,6S)-6-[(1R)-hydroxyethyl]-2-{4-[(2-hydroxyethyl-1pyridinio)methyl]phenyl}penem-3-carboxylate (Compound 57); (5R,6S)-6-[(1R)-hyroxyethyl]-2-{4-[(8-hydroxy-1quinolinio)methyl]phenyl}penem-3-carboxylate (Compound 58);

(5R,6S)-6-[(1R)-hydroxyethyl]-2-{4-[(8-hydroxy-2isoquinolinio)methyl]phenyl}penem-3-carboxylate (Compound 59);

(5R,6S)-6-[(1R)-hydroxyethyl]-2-{4-[(3-formylamino-1pyridinio)methyl]phenyl}penem-3-carboxylate (Compound 60);

(5R,6S)-6-[(1R)-hydroxyethyl]-2-{4-[(4-hydroxyaminocarbonyl-1-pyridinio)methyl]phenyl}penem-3-carboxylate (Compound 61);

(5R,6S)-6-[(1R)-hydroxyethyl]-2-{4[(3-formyl-1pyridinio)methyl]phenyl}penem-3-carboxylate (Compound 62);

(5R,6S)-6-[(1R)-hydroxyethyl]-2-{4-[(3-hydroxyiminomethyl-1-pyridinio)methyl]phenyl}penem-3carboxylate (Compound 63);

(5R,6S)-6-[(1R)-hydroxyethyl]-2-{4-{4-[(1-hydroxyiminoethyl)-1-pyridinio]methyl}phenyl}penem-3-carboxylate (Compound 64);

(5R,6S)-6-[(1R)-hydroxyethyl]-2-{4-[(3-amino-1pyridinio)methyl]phenyl}penem-3-carboxylate (Compound 65);

(5R,6S)-6-[(1R)-hydroxyethyl]-2-{4-[(1pyrazinio)methyl]phenyl}penem-3-carboxylate (Compound 66);

(5R,6S)-6-[(1R)-hydroxyethyl]-2-{4-[(1-methyl-1triazolio)methyl]phenyl}penem-3-carboxylate (Compound 67);

(5R,6S)-6-[(1R)-hydroxyethyl]-2-{4-[(2-methyl-1pyrazolio)methyl]phenyl}penem-3-carboxylate (Compound 68);

(5R,6S)-6-[(1R)-hydroxyethyl]-2-{4-[(thieno[2,3-c]pyridinio)methyl]phenyl}penem-3-carboxylate (Compound 69);

(5R,6S)-6-[(1R)-hydroxyethyl]-2-{4-[(furo[2,3c-]pyridinio)methyl]phenyl}penem-3-carboxylate (Compound 70);

(5R,6S)-6-[(1R)-hydroxyethyl]-2-{4-[(furo[3,2c-]pyridinio)methyl]phenyl}penem-3-carboxylate (Compound 71);

(5R,6S)-6-[(1R)-hydroxyethyl]-2-{4-[(thieno[3,2c-]pyridinio)methyl]phenyl}penem-3-carboxylate (Compound 72);

(5R,6S)-6-[(1R)-hydroxyethyl]-2-{4-[(thieno[2,3b-]pyridinio)methyl]phenyl}penem-3-carboxylate (Compound 73);

(5R,6S)-6-[(1R)-hydroxyethyl]-2-{4-[(furo[2,3b-]pyridinio)methyl]phenyl}penem-3-carboxylate (Compound 74);

(5R,6S)-6-[(1R)-hydroxyethyl]-2-{4-[(thieno[3,4c-]pyridinio)methyl]phenyl}penem-3-carboxylate (Compound 75); and (5R,6S)-6-[(1R)-hydroxyethyl]-2-{4-[(thiazolo[4,5c-]pyridinio)methyl]phenyl}penem-3-carboxylate (Compound 76).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of the formula I

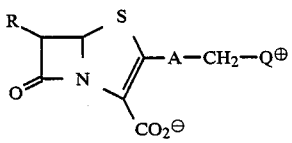

wherein

R is $C_1$-$C_4$ alkyl substituted by at least one substituent selected from the group consisting of free hydroxyl groups and protected hydroxy groups;

A is —Z—, Z—O—CO— or —Z—CO, wherein:

Z represents:
  (a) phenylene;
  (b) thiophenediyl;
  (c) $C_2$-$C_4$ alkenylene;
  (d) an unsubstituted $C_3$-$C_8$ cycloalkylene ring;
  (e) an aralkylene radical of formula

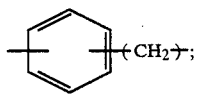

and

Q+ represents a +$NR_1R_2R_3$ group, wherein
  (i) $R_1$, $R_2$ and $R_3$ are each independently unsubstituted $C_1$-$C_4$ alkyl, or $R_1$, $R_2$ and $R_3$ are each independently $C_1$-$C_4$ alkyl substituted by —$NR_4R_5$, wherein $R_4$ and $R_5$ are, independently, hydrogen or —$CO_2R_4$; or
  (ii) $R_1$ is as defined above under (i) and $R_2$ and $R_3$ together with the nitrogen atom to which they are both bound are an unsubstituted heterocyclyl group selected from the group consisting of:

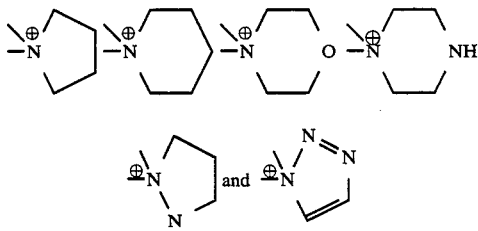

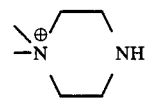

or $R_2$ and $R_3$ together with the nitrogen atom to which they are both bound is a substituted

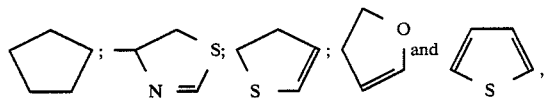

wherein said substituent is at least one $C_1$-$C_4$ alkyl; or (iii) $R_1$, $R_2$ and $R_3$ together with the nitrogen to which they are all bound represent an unsubstituted azoniabicyclo or azoniatricyclo group, or (iv) $R_1$, $R_2$ and $R_3$ together with the nitrogen atom to which they are all bound represent unsubstituted pyridinium, pyrazinium, pyrazolium, or unsubstituted pyridinium, fused with one phenyl ring or with a 5- or 7-membered, saturated or unsaturated cycloaliphatic or heterocyclic ring selected from the group consisting of:

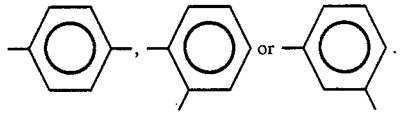

; or (v) $R_1$, $R_2$ and $R_3$ together with the nitrogen atom to which they are all bound represent substituted pyridinium, wherein the substituent is at least one member selected from the group consisting of hydroxy; $C_1$-$C_4$ alkoxys; $C_1$-$C_4$ alkylthios; —$NR_4R_5$, wherein $R_4$ and $R_5$ are hydrogen; —$CO_2R_4$; —CO—$NR_4R_5$; hydroxyiminomethyl (HO—N=CH—); hydroxymino (α-methyl)methyl (HO—N=C(CH₃)—); formamido; $C_1$-$C_4$ alkanoyl; and $C_1$-$C_4$ alkyl which is unsubstituted or is substituted by cyano, sulfo, hydroxy, or $CO_2R_4$; or (vi) $R_1$, $R_2$ and $R_3$ together with the nitrogen atom to which they are all bound represent hydroxy substituted pyridinium fused with one phenyl ring; or a pharmaceutically or veterinarily acceptable salt thereof.

2. The compound of claim 1, wherein R is an (α-hydroxy)ethyl group.

3. The compound of claim 2, wherein Z is a group of the formulae

4. The compound of claim 1, said compound being
(5R,6S)-6-(1R)-hydroxyethyl-2-[4-(N,N,N-trime-
thylammoniomethyl)phenyl]penem-3-carboxylate;
(5R,6S)-6-[(1R)-hydroxyethyl-2-4-(N,N,N-triethylam-
moniomethyl)phenyl]penem-3-carboxylate;
(5R,6S)-6-(1R)-hydroxyethyl]-2-2-(N,N,N-trime-
thylammoniomethyl)phenyl]penem-3-carboxylate;
(5R,6S)-6-(1R)-hydroxyethyl]-2-]2-(N,N,N-triethylam-
moniomethyl) phenyl]penem-3-carboxylate, or
(5R,6S)]-6-(1R)-hydroxyethyl]-2-[3-(N,N,N-trime-
thylammoniomethyl) phenyl]penem-3-carboxylate.

5. The compound of claim 3, wherein $R_1$, $R_2$ and $R_3$ taken together with the nitrogen atom to which they are all bound represent one of the following radicals

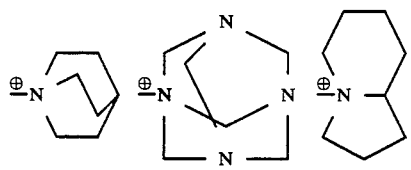

wherein the quinuclidine ring is unsubstituted or substituted by an oxo, hydroxy or methoxy group.

6. The compound of claim 5, said compound being
(5R,6S)-6-[(1R)-hydroxyethyl]-2-[4(quinuclidiniome-
thyl)phenyl]penem-3-carboxylate.

7. The compound of claim 1, said compound being
(5R,6S)-6-[(1R)-hydroxyethyl]-2-[1-(pyridiniomethyl)-
cyclopentyl]penem-3-carboxylate;
(5R,6S)-6-(1R)-hydroxyethyl]-2-[1-(N-methylpyr-
rolidiniomethyl)cyclopentyl]penem-3-carboxylate;
(5R,6S)-6-[(1R)-hydroxyethyl]-2-[1-(N,N,N-triethylam-
moniomethyl) cyclopentyl]penem-3-carboxylate;
(5R,6S)-6-[(1R)-hydroxyethyl]-2-[3-(N,N,N-trime-
thylammoniomethyl) cyclobutyl]penem-3-carboxy-
late; or
(5R,6S)-6-[(1R)-hydroxyethyl]-2-[3(pyriliniomethyl)cy-
clopentyl penem-3-carboxylate.

8. The compound of claim 1, said compound being
(5R,6S)-6-[(1R)-hydroxyethyl]-2-[(E)-2-(pyridiniome-
thyl)ethenyl]penem-3-carboxylate;
(5R,6S)-6-[(1R)-hydroxyethyl]-2-[(Z)-2-(pyridiniome-
thyl)ethenyl]penem-3-carboxylate; or
(5R,6S)-6-[(1R)-hydroxyethyl]-2-[(Z)-2-(N-methylpyr-
rolidiniomethyl) ethenyl]penem-3-carboxylate.

9. The compound of claim 2, wherein Z is a group of the formula

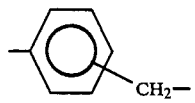

10. The compound of claim 9, said compound being
(5R,6S-6-[(1R)-hydroxyethyl]-2-[4-(2-oxo-3pyridinio-
propyl)phenyl]penem-3-carboxylate.

11. A pharmaceutical or veterinary antibacterial composition comprising:
(i) an inert carrier or diluent; and,
(ii) a pharmaceutically or veterinarily effective amount of at least one compound of claim 1 or a pharmaceutically or veterinarily acceptable salt thereof.

12. A method for combating bacteria, comprising administering to a human or animal in need thereof, an antibacterially effective amount of at least one compound of claim 1 or a pharmaceutically or veterinarily acceptable salt thereof.

13. The method of claim 12, said method comprising combating Gram-positive bacteria.

14. The method of claim 12, said method comprising combating Gram-negative bacteria.

15. A method for combating a respiratory tract infection, comprising administering to a human or animal in need thereof an amount of at least one compound of claim 1 or a pharmaceutically or veterinarily acceptable salt thereof, effective for combating the said respiratory tract infection.

16. The method of claim 15, comprising combating bronchitis, bronchopneumonia or pleuritis.

17. A method for combating a hepatobiliary infection, comprising administering to a human or animal in need thereof an amount of at least one compound of claim 1 or a pharmaceutically or veterinarily acceptable salt thereof, effective for combating the said hepatobiliary infection.

18. A method for combatting an abdominal infection, comprising administering to a human or animal in need thereof an amount of at least one compound of claim 1 or a pharmaceutically or veterinarily acceptable salt thereof effective for combatting the said abdominal infection.

19. A method for combatting septicemia, thereof an amount of at least one compound of claim 1 or a pharmaceutically or veterinarily acceptable thereof, effective for combatting the said septicemia.

20. A method of combatting a urinary tract infection, comprising administering to a human or animal in need thereof an amount of at least one compound of claim 1 or a pharmaceutically or veterinarily acceptable salt thereof, effective for combatting the said urinary tract, infection.

21. The method of claim 20, comprising combatting pyelonephritis or cystitis.

22. A method for combatting an obstetrical infection, comprising administering to human or animal in need thereof an amount of at least one compound of claim 1 or a pharmaceutically or veterinarily acceptable salt thereof, effective for combatting the said obstetrical infection.

23. A method for combatting a gynecological infection, comprising administering to human or animal in need thereof an amount of at least one compound of claim 1 or a pharmaceutically or veterinarily acceptable salt thereof, effective for combatting the said gynecological infection.

24. The method of claim 23, comprising combatting cervicitis or endometritis.

25. A method for combatting an ear, nose or throat infection, comprising administering to a human or an animal in need thereof an amount of at least one compound of claim 1 or a pharmaceutically or veterinarily acceptable salt thereof, effective for combatting the said ear, nose or throat infection.

26. The method of claim 2, comprising combatting otitis, sinusitis or parotitis.

* * * * *